United States Patent [19]

Norval

[11] 4,323,699

[45] Apr. 6, 1982

[54] OXIDATION OF SUBSTITUTED AROMATIC COMPOUNDS TO AROMATIC CARBOXYLIC ACIDS

[75] Inventor: Stephen V. Norval, Guisborough, England

[73] Assignee: Imperial Chemical Industries Limited, London, England

[21] Appl. No.: 267,421

[22] Filed: May 26, 1981

[30] Foreign Application Priority Data

Jun. 10, 1980 [GB] United Kingdom ............... 18919/80

[51] Int. Cl.³ ............................................. C07C 51/16
[52] U.S. Cl. ..................................... 562/416; 562/421
[58] Field of Search ................................ 562/416, 421

[56] References Cited

U.S. PATENT DOCUMENTS 3,678,106 7/1972 Ager ..................................... 562/416

FOREIGN PATENT DOCUMENTS 15-24451 10/1940 Japan ................................... 562/416
18-11444 5/1943 Japan ................................... 562/416

Primary Examiner—Alan Siegel
Attorney, Agent, or Firm—Cushman, Darby & Cushman

[57] ABSTRACT

Oxidation of a substituted aromatic compound e.g. p-xylene to an aromatic carboxylic acid e.g. tere-phthalic acid using a heavy metal/bromine catalyst in an aqueous reaction medium in the presence of an iodine promoter.

10 Claims, No Drawings

OXIDATION OF SUBSTITUTED AROMATIC COMPOUNDS TO AROMATIC CARBOXYLIC ACIDS

The present invention relates to the oxidation of substituted aromatic compounds to aromatic carboxylic acids.

Aromatic carboxylic acids such as tere-phthalic acid are important chemical intermediates used, for example in the production of polyesters such as polyethyleneglycolterephthalate. One method of manufacturing the acids is from the equivalent substituted aromatic compound by oxidising the substituent group(s) to carboxyl groups. This oxidation has been carried out for many years by a process which is operated in the liquid phase in which there is used as catalyst a heavy metal, eg a cobalt compound and/or bromine or a bromine-containing compound the reaction medium being acetic acid. The present invention concerns an improvement to this type of process in which water is the reaction medium and iodine or an iodine-containing compound is present as promoter.

According to the invention a process for the production of an aromatic carboxylic acid comprises oxidising by means of molecular oxygen a substituted aromatic compound in the presence of a catalyst comprising a heavy metal compound and/or a bromine or bromine-containing compound characterised in that the reaction is carried out in an essentially aqueous reaction medium and in the presence of iodine or an iodine-containing compound.

The aromatic compound is preferably substituted by an alkyl, hydroxyalkyl or a formyl group. Particularly suitable alkyl groups are lower ($C_1$ to $C_8$) alkyl groups e.g. methyl, ethyl and isopropyl groups. Particularly suitable hydroxyalkyl groups are hydroxymethyl and hydroxyethyl groups. One, two or more such groups may be present in the aromatic nucleus and the groups may be the same or different. The aromatic nucleus may, for example, be a benzene or naphthalene nucleus. Particularly suitable aromatic compounds to be oxidised are toluene, ethylbenzene, isopropylbenzene, o-, m- and p-xylene, cumene, pseudocumene, the isomeric diiopropylbenzenes, durene, mesitylene, hydroxymethylbenzene, hydroxyethylbenzene, bis-hydroxymethylbenzene, benzaldehyde and 2,6-dimethylnaphthalene. Suitable aromatic compounds also include those which are already partially oxidised to carboxylic acids and their corresponding esters, for example, the isomeric tolualdehydes, p-toluic acid, methyl p-toluate and p-carboxybenzaldehyde. The process of our invention is particularly suitable for the oxidation of p-xylene p-tolualdehyde or p-toluic acid to tere-phthalic acid.

The molecular oxygen used in the process may be used alone or in admixture with other gases e.g. as air or as a mixture of oxygen and nitrogen with a higher or lower oxygen content than that of air.

The heavy metals which may be used as catalysts include vanadium, chromium, manganese, iron, cobalt, nickel, molybdenum, a lanthanide e.g. cerium, hafnium and zirconium. Particularly suitable is manganese especially in combination with cobalt and/or with nickel. The amount of the heavy metal present during the oxidation may be subject to wide variation. When manganese and cobalt are the heavy metals the concentration of manganese may be 20 to 20,000 ppm based on solvent and cobalt 10 to 10,000 ppm, the manganese being in excess e.g. up to 20 times the other metals (on an atomic basis). The heavy metals may be used, for example, in the form of their inorganic or organic acid salts especially the bromides or lower ($C_1$ to $C_4$) alkanoates e.g. acetates.

The catalyst may also be bromine or bromine-containing compound which may be used alone or together with a heavy metal catalyst. The bromine may be provided as bromine itself, as hydrogen bromide, as an organic bromine compound e.g. tetrabromoethane or as an inorganic bromide. Suitable bromides include, for example, bromides of the heavy metals when the latter are present, for example manganese or cobalt bromide. The amount of bromine present in the process may vary widely but generally lies in the range 500 to 50,000 ppm based on the weight of solvent. When used with a heavy metal it is preferred that the amount of bromine is in excess of the stoichiometric amount required to form a salt with the metal, especially up to 20:1 bromide to heavy metal (atomic ratio). Preferably the bromine is provided as hydrogen bromide.

The iodine may be provided in the process as iodine itself or as an iodine-containing compound. The iodide-containing compound may be organic e.g. ethyl iodide or inorganic. Preferred inorganic iodine-containing compounds include hydrogen iodide, alkali metal iodides e.g. lithium, sodium and potassium iodide and ammonium iodide. The iodine may also be provided in the form of the iodide of the heavy metal used as catalyst in the process e.g. as manganese and/or cobalt iodide. The amount of iodine or iodine-containing compound present in the process is preferably in the range 0.1 to 1,000 ppm based on the weight of solvent, more preferably 1 to 500 ppm.

The solvent used in the process is essentially water and the ratio of water to substituted aromatic compound lies in the range 2:1 to 100:1.

The oxidation may be effected, for example, at temperatures in the range 200° to 300° C. preferably 210° to 260° C. Pressures are at least such that a liquid phase is maintained in the reactor, and are, for example up to 200 bar preferably 15 to 150 bar.

The separation and purification of the aromatic dibasic acid product of the process may be carried out by known means. Thus the product may be cooled, separated by filtration or by centrifuging and washed with fresh solvent. It may also be subject to a secondary or post-oxidation to improve its quality and/or it may be catalytically hydrogenated in the presence of a catalyst e.g. platinum to achieve the same object.

The process according to the present invention produces a product which, all other factors being equal, is purer than that produced in the absence of iodine or iodine-containing compound. In particular, the product is characterised by a lower content of partial oxidation products e.g. p-carboxybenzaldehyde in terephthalic acid.

The invention will now be further described with reference to the following examples in which the apparatus used consisted of a titanium autoclave of total capacity 4.5 liters, equipped with a heater, reflux condenser, agitator, gas inlet and outlet, and feed inlet and outlet. The purity of the tere-phthalic acid product of the process described in the Examples was assessed by measuring its 4-carboxybenzaldehyde content, the latter compound being an intermediate oxidation product.

EXAMPLE 1

54g p-toluic acid was charged to the autoclave together with 1800 ml water, 9.2 ml of 47% w/w aqueous HBr, 5.87 g of manganese dibromide tetrahydrate and 6.24 g of cobalt dibromide hexahydrate. The reaction mixture was then heated under a nitrogen atmosphere to 215° C. and a total pressure of 34.5 bar. A mixture of 30% by volume oxygen in nitrogen was then passed through the autoclave at a total flow rate of about 7001 per hour (measured at STP). After 30 minutes oxidation, a small sample of the reaction mixture was removed from the autoclave. The oxidation was continued for a further 30 minutes and another sample of reaction mixture removed from the autoclave. The samples of reaction mixture were cooled to ambient temperature and the product filtered, washed with water and dried. The dried products were analysed and found to contain respectively 3.7% and 1.5% by weight of 4-carboxybenzaldehyde (4CBA).

EXAMPLE 2

Example 1 was repeated except that 0.12 g of potassium iodide was added to the solution. The tere-phthalic acid products were found to contain 0.30% and 0.19% by weight 4CBA respectively after 30 minutes and 60 minutes oxidation.

EXAMPLE 3

The autoclave was charged with 1800 ml water, 10.0 g of manganese dibromide tetrahydrate, 1.88 g of cobalt dibromide hexahydrate and 9.2 ml of 47% w/w aqueous HBr. The reactor contents were heated to 230° at a total pressure of 38 bar under a nitrogen gas flow. A flow of approximately 20% by volume oxygen in nitrogen was then substituted for the nitrogen flow and 250 ml p-tolualdehyde (pTAL) introduced continuously to the reactor over a period of one hour. A sample of the reaction mixture was then removed from the reactor. The pTAL feed to the reactor having ceased, the oxygen and nitrogen flow was maintained for a further 30 minutes while the temperature was maintained at 230° C. Another sample of reaction mixture was then removed from the reactor. The samples of reaction mixture were cooled to ambient temperature, and the product filtered, washed with water and dried. The solid tere-phthalic acid products were found to contain 0.68% by weight of 4CBA and 0.36% by weight of p-toluic acid (pTA) following the initial oxidation period and 0.24% by weight of 4CBA and 0.12% by weight of pTA following the further 30 minute oxidation.

EXAMPLE 4

Example 3 was repeated, except that 0.12 g of potassium iodide was added to the solution. The tere-phthalic acid products were found to contain 0.22% by weight of 4CBA and 0.07% by weight of pTA following the initial oxidation period and 0.09% by weight of 4CBA and 0.03% by weight of pTA following the further 30 minute oxidation.

EXAMPLE 5

The autoclave was charged with 1800 ml water, 10.0 g of manganese dibromide tetrahydrate, 1.88 g of cobalt dibromide hexahydrate 0.12 g potassium iodide, 13.2 ml of 47% by weight aqueous HBr and 90 g of purified tere-phthalic acid. The reactor contents were heated to 230° C. at a total pressure of 38 bar under a nitrogen gas flow. A flow of approximately 20% oxygen in nitrogen was then substituted for the nitrogen flow and 130 ml p-xylene introduced continuously to the reactor over a period of one hour. A sample of the reaction mixture was then removed from the reactor. The p-xylene feed to the reactor having ceased, the oxygen and nitrogen flow was continued for a further 30 minutes while the temperature was maintained at 230° C. Another sample of reaction mixture was then removed from the reactor. The samples of reaction mixture were cooled to ambient temperature and the products filtered, washed with water and dried. The solid tere-phthalic acid products were found to contain 1.8% by weight 4-carboxybenzaldehyde (4CBA) and 1.5% by weight p-toluic acid (pTA) following the initial reaction period and 1.0% by weight 4CBA and 0.64% by weight pTA following the further 30 minute oxidation. (4CBA and pTA are intermediate oxidation products in the conversion of p-xylene to tere-phthalic acid).

EXAMPLE 6

The autoclave was charged with 1800 ml water, 90 g purified terephthalic acid, 10.0 g manganese dibromide tetrahydrate, 1.88 g cobalt dibromide hexahydrate, 0.12 g potassium iodide and 8.9 ml 47% w/w aqueous HBr. The reactor contents were heated to 248° C. at a total pressure of 56 bar under a nitrogen gas flow. A flow of approximately 20% oxygen in nitrogen was then substituted for the nitrogen flow and 62 ml of p-xylene was introduced continuously to the reactor over a period of one hour. The p-xylene flow having ceased, the oxygen and nitrogen flow was continued for a further 30 minutes while the temperature was maintained at 248° C. The reactor contents were then cooled to about 150° C. under nitrogen flow and the solid terephthalic acid product filtered off, washed in water and dried. The 164 g of terephthalic acid recovered contained 0.05% by weight 4CBA and 0.10% by weight pTA.

EXAMPLE 7

The experiment of example 3 was repeated except that the reaction temperature was 245° C. and the total pressure 56 bar. The solid terephthalic acid products were found to contain 0.29% by weight 4CBA and 0.21% by weight pTA following the initial oxidation period and 0.08% by weight 4CBA and 0.07% by weight pTA following the further 30 minute oxidation.

EXAMPLE 8

The experiment of example 7 was repeated except that 0.024 g of potassium iodide was added to the solution. The terephthalic acid products were found to contain 0.15% by weight 4CBA and 0.12% by weight pTA following the initial oxidation period and 0.09% by weight 4CBA and 0.06% by weight pTA following the further 30 minute oxidation.

EXAMPLE 9

The experiment of example 7 was repeated except that 0.12 g of potassium iodide was added to the solution. The terephthalic acid products were found to contain 0.10% by weight 4CBA and 0.10% by pTA following the initial oxidation period and 0.03% by weight 4CBA and 0.04% by weight pTA following the further 30 minute oxidation.

I claim:

1. In a process for the production of an aromatic carboxylic acid which comprises oxidising by means of molecular oxygen a substituted aromatic compound in the presence of a catalyst comprising a heavy metal compound and/or bromine or a bromine-containing compound, the improvement whereby the reaction is carried out in an essentially aqueous reaction medium and in the presence of iodine or an iodine-containing compound.

2. A process according to claim 1 in which the substituted aromatic compound is p-xylene, p-tolualdehyde, p-toluic acid, methyl p-toluate or p-carboxybenzaldehyde.

3. A process according to claim 1 characterised in that the heavy metal compound comprises manganese.

4. A process according to claim 3 in which the heavy metal is manganese in combination with cobalt and/or with nickel.

5. A process according to claim 1 in which the bromine-containing compound is hydrogen bromide or a bromide of the heavy metal used in the process.

6. A process according to claim 1 in which the iodine-containing compound is hydrogen iodide, an alkali metal iodide, ammonium iodide or an iodide of the heavy metal used in the process.

7. A process according to claim 1 in which the amount of iodine or iodine-containing compound present in the process is in the range 0.1 to 1,000 ppm based on the weight of solvent.

8. A process according to the claim 1 in which the process is carried out at a temperature in the range 200° to 300° C.

9. A process according to claim 8 in which the temperature is in the range 210° to 260° C.

10. A process according to claim 1 in which the substituted aromatic compound is p-xylene, p-tolualdehyde or p-toluic acid, the temperature is 210° to 260° C., the catalyst is manganese optionally with one or more heavy metals, the bromine-containing compound is hydrogen bromide or the bromide of one or more of the heavy metals and the iodine-containing compound is hydrogen iodide, lithium iodide, sodium iodide, potassium iodide, ammonium iodide or the iodide of one or more of the heavy metals.

* * * * *